United States Patent
Stabile et al.

(10) Patent No.: US 9,428,486 B1
(45) Date of Patent: Aug. 30, 2016

(54) EFFICIENT PROCESS FOR THE PREPARATION OF ESOMEPRAZOLE (S)-BINOL COMPLEX

(71) Applicant: F.I.S. - Fabbrica Italiana Sintetici S.p.A., Montecchio Maggiore (IT)

(72) Inventors: Paolo Stabile, Verona (IT); Moreno Bertolazzi, Costalunga (IT); Nicola Faccin, Valdagno (IT); Diego Rasia, Trissino (IT)

(73) Assignee: F.I.S.—Fabbrica Italiana Sintetici S.p.A., Montecchio Maggiore (IT)

( * ) Notice: Subject to any disclaimer, the term of this patent is extended or adjusted under 35 U.S.C. 154(b) by 0 days.

(21) Appl. No.: 14/745,481

(22) Filed: Jun. 22, 2015

(30) Foreign Application Priority Data

Jul. 29, 2014 (EP) ..................................... 14178889

(51) Int. Cl.
*C07D 401/00* (2006.01)
*C07D 401/12* (2006.01)
*C07C 37/00* (2006.01)

(52) U.S. Cl.
CPC .............. *C07D 401/12* (2013.01); *C07C 37/00* (2013.01); *C07B 2200/07* (2013.01)

(58) Field of Classification Search
None
See application file for complete search history.

(56) References Cited

U.S. PATENT DOCUMENTS 8,404,853 B2 * 3/2013 Singh .................. C07D 401/12
546/273.7

FOREIGN PATENT DOCUMENTS

| CN | 1087739 C | 7/2002 | |
|---|---|---|---|
| EP | 0 652 872 B1 | 11/2000 | |
| EP | WO 2006094904 A1 * | 9/2006 | ........... C07D 401/12 |
| EP | 2 980 086 A1 | 2/2016 | |
| WO | WO 96/02535 A1 | 2/1996 | |
| WO | WO 2006/040635 A1 | 4/2006 | |
| WO | WO 2006/094904 A1 | 9/2006 | |
| WO | WO2007-013743 A1 | 2/2007 | |
| WO | WO 2007/013743 A1 | 2/2007 | |
| WO | WO 2012/104863 A2 | 8/2012 | |
| WO | WO2012-104863 A2 | 8/2012 | |

OTHER PUBLICATIONS

Extended European Search Report for EP Application No. 14178889.3, European Patent Office, Munich, Germany, dated Oct. 29, 2014, 4 pages.
Deng, J.. et al., "Resolution of omeprazole by inclusion complexation with a chiral host BINOL," *Tetrahedron: Asymmetry* 11:1729-1732, Elsevier Science Ltd., England (2000).

* cited by examiner

*Primary Examiner* — Heidi Reese
(74) *Attorney, Agent, or Firm* — Sterne, Kessler, Goldstein & Fox P.L.L.C.

(57) ABSTRACT

Object of the present invention is an improved process for the preparation of Esomeprazole (S)-BINOL complex which is a key intermediate for the synthesis of Esomeprazole and salts thereof.

15 Claims, No Drawings

EFFICIENT PROCESS FOR THE PREPARATION OF ESOMEPRAZOLE (S)-BINOL COMPLEX

CROSS-REFERENCE TO RELATED APPLICATIONS

This Patent Application claims priority to and benefit of European Patent Application No. EP14178889.3 filed on Jul. 29, 2014, the contents of the which are incorporated herein by reference.

TECHNICAL FIELD

Object of the present invention is an efficient process for the synthesis of Esomeprazole (S)-(−)-Binol complex.

STATE OF THE ART

Esomeprazole is the (S)-enantiomer of the racemic compound and active pharmaceutical ingredient named Omeprazole and, as Omeprazole, is itself an active ingredient classified as proton pump inhibitor.

Esomeprazole is thus also named (S)-(−)-Omeprazole or simply (S)-Omeprazole.

Esomeprazole has the following structural chemical formula (II):

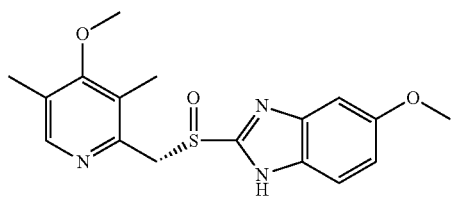

(II)

wherein the sulfur atom is the asymmetric center that provides chirality to the molecule.

Omeprazole, a compound consisting of a racemic mixture of the enantiomers (S)-Omeprazole and (R)-Omeprazole, has the following structural formula (III):

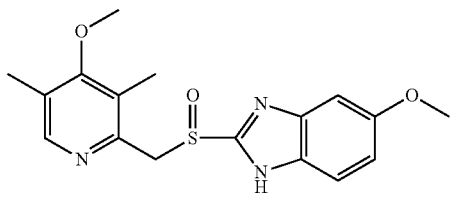

Other active pharmaceutical ingredients belonging to the same therapeutic category and to the family of the "Prazoles" are, for example, the following: Lansoprazole, Dexlansoprazole, Pantoprazole, Rabeprazole, Picoprazole, Iraprazole etc.

All the aforementioned active substances act limiting acid gastric secretion.

Esomeprazole currently present on the market is characterized by specific solid forms which are Esomeprazole Magnesium trihydrate having stoichiometry (2:1:3) and Esomeprazole sodium salt (1:1).

Esomeprazole is characterized by an 1H-benzimidazolic heterocyclic system, by a (pyridin-2-yl)methyl group and by an optically active sulphoxyde group, in particular, having S configuration and providing negative optical rotation.

Said chemical groups constitute the skeleton of all active pharmaceutical ingredients belonging to the family of Prazoles which therefore differ each other in the substituents of both the aromatic systems and for the sulphoxyde group which can be or not optically active.

Chemical names that define Esomeprazole are 1H-Benzimidazole, 5-methoxy-2-[(S)-[(4-methoxy-3,5-dimethyl-2-pyridinyl)methyl]sulfinyl]- or 5-methoxy-2-[(S)-[(4-methoxy-3,5-dimethyl-2-pyridinyl)methyl]sulfinyl]-1H-benzimidazole.

A known process for the synthesis of Esomeprazole is disclosed in the application EP652872 and comprises the separation of diasteromeric derivatives of Omeprazole, separated by means of chromatography or by fractional crystallization. The efficiency of said process is intrinsically very limited.

The process disclosed in WO9602535 is based on an efficient enantioselective oxidation of prochiral heterocyclic sulfide carried out by means of chiral complexes of titanium and in presence of a base. The typical conditions of the process imply the use of titanium isopropoxyde, L-(+)-diethyltartrate and cumene hydroperoxide. This process provides enriched mixtures of optical isomers of Omeprazole having ratio of (S)-Omeprazole to (R)-Omeprazole higher than 90:10 (weight/weight).

In the recent years a new technology for the preparation of Esomeprazole has been developed with the aim of preparing Esomeprazole at low industrial costs. Said technology is based on the optical resolution of Omeprazole mediated by chiral hosts, such as for example L-(+)-diethyltartrate as disclosed in WO2006040635 or other chiral ligands.

In particular, the optical resolution of the racemic compound Omeprazole is carried out by means of the formation and isolation of Esomeprazole (S)-(−)-BINOL complex, also named Esomeprazole (S)-BINOL complex, having the following formula (I):

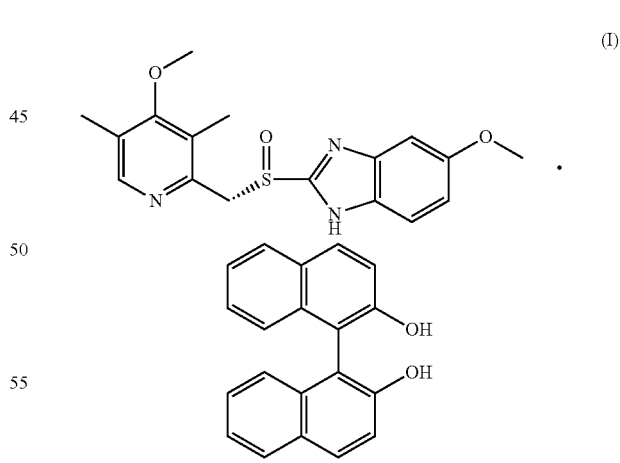

(I)

It is well known and described in the literature that Esomeprazole (S)-(−)-BINOL complex is an inclusion complex which can be well suitable as a key intermediate for the preparation of Esomeprazole and salts thereof, such as, for example, Esomeprazole Magnesium triihydrate or Esomeprazole sodium.

The synthesis of Esomeprazole (S)-(−)-BINOL complex by reaction of Omeprazole with (S)-(−)-BINOL followed by the isolation of this complex as solid, allows the separation of the S isomer, i.e. Esomeprazole, from the other isomer, (R)-Omeprazole, which remains in the mother liquors.

Esomeprazole (S)-(−)-BINOL complex was first disclosed by Deng J. et al. in Tetrahedron: Asymmetry (2000), 1729-1732. Said Esomeprazole (S)-(−)-BINOL complex was prepared at 110° C. from Omeprazole in 36 volumes of a solvent mixture benzene:hexane (v/v=4:1), using 1.5 molecular equivalents of (S)-(−)-BINOL and obtaining the product with molar yield 92.4% based on a half of Omeprazole and the product being a grey-blue powder with 90.3% of e.e. The product was then recrystallized from benzene:hexane (v/v 1:1).

The measure expressed in volumes of solvents, as described in the present application is always referred to the amount of Omeprazole; thus, for example, 10 ml of solvent per 5 g of Omeprazole, correspond to 2 volumes of solvent.

The same author disclosed the preparation of Esomeprazole (S)-(−)-BINOL complex in the Chinese patent publication CN1087739 wherein said preparation was carried out at 80-110° C. and using one or more solvents chosen between benzene, methylbenzene, xylene, mesitylene in combination with normal hexane and obtaining similar results.

In the later patent publication WO2006/094904, example 1, Esomeprazole (S)-(−)-BINOL complex was prepared from Omeprazole in a mixture of 9.6 volumes of toluene and 2.4 volumes of heptane plus 0.2 volumes of triethylamine, using 1.5 molecular equivalents of (S)-(−)-BINOL at 70° C. for 30 minutes, achieving a product with 97% e.e. with 94% molar yield. In example 2 the same preparation was carried out but using only 8 volumes of toluene instead of 9.6 volumes of toluene plus 2.4 volumes of heptane. According to the description, the presence of the amine provided the effect of increasing the optical purity of the product isolated, nevertheless, it would be convenient for an industrial process to avoid, when possible, the use of amines.

In the PCT application WO2007/013743, examples 1-14, Esomeprazole (S)-(−)-BINOL complex was prepared at 60° C. from Omeprazole in mixtures of alcohols and water or from mixtures acetone/water, acetonitrile/water, 1,4-dioxane/water, always in presence of ammonia or triethylamine and using 0.60 molecular equivalents of (S)-(−)-BINOL. The product achieved an optical purity, in terms of e.e., ranging from 95.0% to 98.8%. Nevertheless, nothing is said about the chemical purity of the product except for the fact that the product is white-yellow instead being black as prepared by prior art comparative examples.

In U.S. Pat. No. 8,404,853, example 1, Esomeprazole (S)-(−)-BINOL complex was prepared from Omeprazole at 50-55° C. for 30-45 minutes in a mixture of 16 volumes of toluene plus 4 volumes of cyclohexane and in absence of a base. The product was obtained with 85% yield and 99.5% e.e.

At last, in WO2012/104863, example 2, the preparation of Esomeprazole (S)-(−)-BINOL complex was carried out from Omeprazole at room temperature for 15 minutes in 2.5 volumes of methylene chloride, using 1.09 molecular equivalents of (S)-(−)-BINOL, and adding 14.8 volumes of toluene. Nothing is said about the chemical purity and optical purity of the product obtained. The molar yield of this process, referred only to half of the Omeprazole, i.e. in terms of Esomeprazole, was 83.7%.

During the experimentation in our R&D Labs with the aim to prepare Esomeprazole (S)-(−)-BINOL complex from Omeprazole we observed that, replicating the prior art methods for R&D purposes, one of the biggest problem was the relatively low chemical purity of the product.

Such a problem is also confirmed by the fact that most of the known methods for the preparation of Esomeprazole (S)-(−)-BINOL complex are followed by procedure directed to the re-crystallization/purification of the product.

The chemical purity of Esomeprazole (S)-(−)-BINOL complex depends indeed by two factors: the first being the chemical purity of Omeprazole used as starting material and the second being the process of preparation of Esomeprazole (S)-(−)-BINOL complex itself. The formation of organic impurities during the preparation of Esomeprazole (S)-(−)-BINOL decreases indeed the chemical purity of the product.

Regarding the first factor, i.e. the chemical purity of Omeprazole starting material, three impurities are known and are hereafter described.

One relevant impurity of Omeprazole is Omeprazole N-Oxide having the following structure:

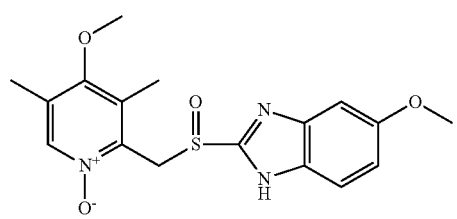

The impurity Omeprazole N-oxide such as, or as Esomeprazole N-oxide is also an impurity of the product Esomeprazole (S)-(−)-BINOL complex.

Another very important Omeprazole impurity is the impurity named Sulfone, having the following chemical structure:

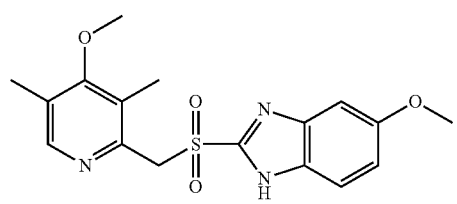

It has been observed that most of the prior art methods do not remove efficiently this important impurity of Esomeprazole, which is an impurity difficult to be removed from the product so that it remains in the final product Esomeprazole Magnesium trihydrate or Esomeprazole sodium.

The last impurity of Omeprazole is named Ufiprazole and it is the typical starting material used for the synthesis of Omeprazole by oxidation or used for the synthesis of Esomeprazole by asymmetric oxidation.

Ufiprazole has the following structure:

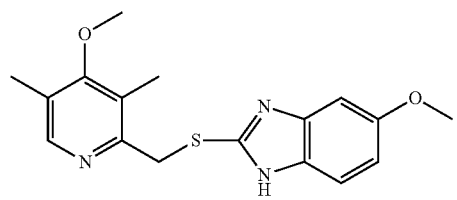

With reference to the second factor, i.e. the impurities that arises during the process for the preparation of Esomeprazole (S)-(−)-BINOL complex, two impurities have to be considered as hereafter described.

It has been experimentally observed repeating the known processes, that the amount of the impurity Esomeprazole N-oxide, as described above, increases during the preparation of Esomeprazole (S)-(−)-BINOL complex. This can be due to oxidation phenomena that occur during the preparation of the complex.

Finally, replicating the prior art methods it has been observed that not all of them provide Esomeprazole (S)-(−)-BINOL complex having stoichiometry 1:1, but often the product contains an additional amount of (S)-(−)-BINOL. Said (S)-(−)-BINOL is not part of the complex, and cannot be considered as part of the complex having a different stoichiometry, but said excess of (S)-(−)-BINOL simply constitutes an impurity of the product.

SUMMARY OF INVENTION

The problem addressed by the present invention is therefore that of providing an improved process for the preparation Esomeprazole (S)-(−)-BINOL complex which allows to prepare such compound:
with higher chemical purity and, in particular,
  a. efficiently removing or reducing the Sulfone, the Ufiprazole and the N-oxide impurities,
  b. avoiding the formation of the N-oxide impurity,
  having the correct amount of (S)-(−)-BINOL, i.e. avoiding the (S)-(−)-BINOL impurity,
while keeping good optical purity and high molar yields.

This problem is solved by a process as outlined in the annexed claims, whose definitions are integral part of the present description.

Further features and advantages of the process according to the invention will result from the description hereafter reported of examples of realization of the invention, provided as an indication and not as a limitation of the invention.

DESCRIPTION OF EMBODIMENTS

Object of the present invention is a process for the preparation of Esomeprazole (S)-(−)-BINOL complex of formula (I):

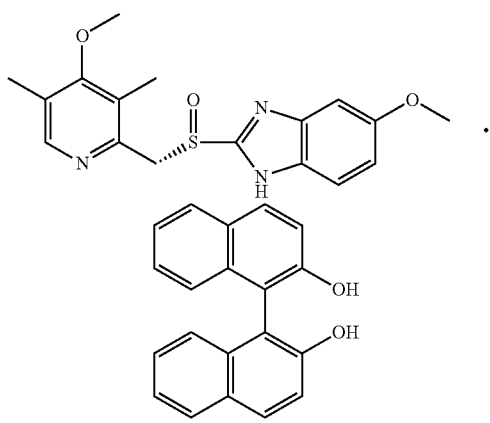

comprising the following steps:
A. providing a mixture of the optical isomers of the compound of formula (III):

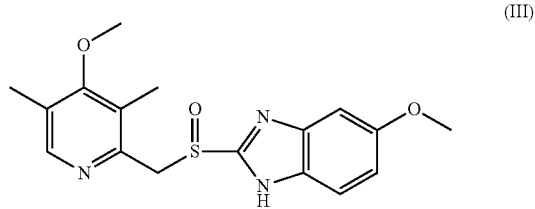

wherein the chiral center is on the sulfur atom,
in dichloromethane;
B. adding to the mixture of the step A from 0.8 to 3.0 molar equivalents of (S)-(−)-Binol;
C. adding an ethereal solvent containing from 5 to 10 atoms of carbon.
D. stirring;
E. isolating Esomeprazole (S)-(−)-BINOL complex of formula (I).

It has been indeed surprisingly found that it is possible to prepare Esomeprazole (S)-(−)-BINOL complex having a high degree of chemical purity, i.e. having a very low content of impurities, also including impurities difficult to be removed such as the sulfone impurity, by addition of an ethereal solvent containing from 5 to 10 atoms of carbon to a solution of dichloromethane containing Esomeprazole (S)-(−)-BINOL complex.

The ethereal solvent containing from 5 to 10 atoms of carbon can be linear or cyclic, and can be for example, methyl-t-buthylether (abbreviated MTBE), diisopropylether (IPE), methylisobuthylether, dibuthylether (DBE), cyclopentyl methyl ether (CPME), methyl-tetrahydrofurane, diisobuthyether, n-buthylmethylether, pentylmethylether, tert-amylmethylether, etc.

In the step A. the mixture of the optical isomers of the compound of formula (III):

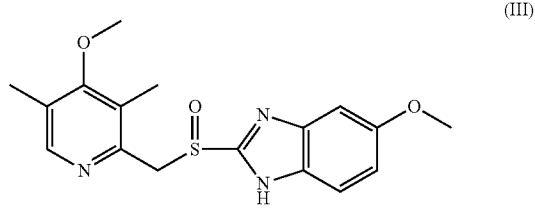

includes the racemic mixture, which is the Omeprazole, and extends from a ratio of 1:99 to 99:1 (weight/weight) of (S)-Omeprazole (i.e. Esomeprazole) versus (R)-Omeprazole. Said mixture of the optical isomers of the compound of formula (III), thus, also includes Esomeprazole comprising 1% or more (weight/weight) of (R)-Omeprazole.

According to a preferred embodiment, the mixture of the optical isomers of the compound of formula (III) having a ratio from 60:40 to 90:10 of (S)-Omeprazole versus (R)-Omeprazole is preferred since it provides the bigger amounts of Esomeprazole (S)-(−)-BINOL complex and since such enantiomerically enriched mixtures of (S)-Omeprazole are those typically prepared using asymmetric oxidation processes. More preferably, the mixture of the optical isomers of the compound of formula (III) having a ratio 80:20 of (S)-Omeprazole versus (R)-Omeprazole can be used in the step A. of the present invention.

The mixture of the optical isomers of the compound of formula (III) of the step A is in contact with dichloromethane, also named methylene chloride, and typically is in form of a suspension but could also be a solution when many volumes of dichloromethane are used.

According to a preferred embodiment, the mixture of the optical isomers of the step A is suspended in an amount of dichloromethane from 2 to 10 volumes, and preferably from 4 to 6 volumes, referred to the compound of formula (III) since these preferred amounts of solvent provide the complete solubilization of the product obtained after the addition of (S)-(−)-BINOL to the mixtures of the optical isomers of the compound of formula (III). Preferably the mixture comprises about 5 volumes of dichloromethane.

According to a preferred embodiment of the process of the present invention in the step B are added from 0.8 to 1.8 molar equivalents of (S)-(−)-BINOL, more preferably are added from 0.9 to 1.6 molar equivalents of (S)-(−)-BINOL, again more preferably, about 1.5 molar equivalents of (S)-(−)-BINOL are added, with reference to the mixture of the optical isomers of the compound of formula (III).

The measure of molar equivalents of (S)-(−)-BINOL reported in the present invention is always referred to the mixture of the optical isomers of the compound of formula (III) and not to the single (S)-isomer, Esomeprazole. Thus, for example 1.5 molar equivalents of (S)-(−)-BINOL means 1.5 mole of (S)-(−)-BINOL per 1 mole of mixture of the optical isomers of the compound of formula (III), for example per 1 mole of Omeprazole.

According to a preferred embodiment of the process of the present invention, after having carried out the step B, the mixture is left under stirring at a temperature comprised between 0° C. and 40° C.

More preferably, the stirring is carried out at a temperature comprised from 15° C. to 25° C.

According to a preferred embodiment of the process of the present invention, after having carried out the step B, the stirring is carried out for a time comprised between 5 and 60 minutes, preferably for about 10 minutes. It has been indeed observed that the complete solubilization of both the reactants, i.e. of the mixture of enantiomers of formula (III) and the (S)-(−)-BINOL, and the solubilization of the product Esomeprazole (S)-(−)-BINOL complex improve the quality of the final product, both in terms of chemical and optical purity.

It should be indeed observed that using from 4 to 6 volumes of solvent referred to the compound of formula (III) the solubilization of the enantiomers mixture of formula (III) in dichloromethane occurs only after the addition of the (S)-(−)-BINOL.

According to a preferred embodiment of the process of the present invention, in the step C are added from 4 to 20 volumes of ethereal solvent referred to the compound of formula (III), more preferably from 4 to 6 volumes of ethereal solvent. Preferably are added about 5 volumes of an ethereal solvent since it provides the best compromise between isolated molar yield and chemical/optical purity of the product.

According to a preferred embodiment of the process of the present invention, the step D is carried out a temperature comprised between 0° C. and 40° C.

According to a more preferred embodiment, in the step D, the mixture is stirred at a temperature comprised in the range from 15° C. to 25° C.

According to a preferred embodiment, in the step D the mixture is stirred for a time comprised between 1 and 4 hours.

According to a preferred embodiment, in the process of the present invention the steps B, C and D are carried out at the same temperature. Preferably all the steps are carried out between 15 and 25° C.

According to an alternative preferred embodiment of the process of the present invention the steps A and B are both carried out at a temperature comprised between 15° C. and 25° C., and the steps C and D are both carried out at a temperature comprised between 15° C. and 25° C. or at a temperature comprised between 0° C. and 5° C.

According to a preferred embodiment of the process of the present invention, the mixture of the optical isomers of the step A is suspended in an amount of solvent from 4 to 6 volumes of dichloromethane and in the step C are added from 4 to 6 volumes of ethereal solvent with reference to the compound of formula (III).

According to a more preferred embodiments of the process of the present invention, the mixture of the optical isomers of the step A is suspended in about 5 volumes of dichloromethane and in the step C are added about 5 volumes of ethereal solvent referred to the compound of formula (III).

According to all the embodiments of the process of the present invention, in the step C, the ethereal solvent containing from 5 to 10 atoms of carbon can be linear or cyclic, and can be for example, methyl-t-buthylether (abbreviated MTBE), diisopropylether (IPE), methylisobuthylether, dibuthylether (DBE), cyclopentyl methyl ether (CPME), methyl-tetrahydrofurane, diisobuthylether, n-buthylmethylether, pentylmethylether, tert-amylmethylether, etc.

Preferably the solvent is chosen between methyl-t-buthylether and cyclopentyl methyl ether since these solvents provide better results in terms of chemical purity of the product and provide, at the same time, a product with high optical purity.

In particular, it is preferred the process where in the step C the ethereal solvent is cyclopentyl methyl ether and the steps C and D are carried out at 20-25° C., since it provides excellent results (see table 1, entry 6).

According to a preferred embodiment of the present invention, when the mixture of the optical isomers of the step A is suspended in an amount of solvent from 4 to 6 volumes of dichloromethane and in the step C are added from 4 to 6 volumes of ethereal solvent with reference to the compound of formula (III), it is preferable to add in the step B at least 1.20 molecular equivalents of (S)-(−)-BINOL, more preferably about 1.50, since it provides the better results in terms of chemical purity, optical purity and molar yield.

According to a preferred embodiment of the present invention the step A is performed using about 5 volumes of dichloromethane, the step B using about 1.5 molecular equivalents of (S)-(−)-BINOL at 20-25° C., the step C, at 20-25° C., using about 5 volumes or MTBE or cyclopentylmethylether.

The product Esomeprazole (S)-(−)-BINOL complex is isolated in the step E by filtration or centrifugation and then can be conveniently dried under vacuum at low temperature (e.g. 35° C.).

Esomeprazole (S)-(−)-BINOL complex is a key intermediate for the synthesis of Esomeprazole and salts thereof and can be converted to Esomeprazole free acid or converted (directly or not) to Esomeprazole Magnesium trihydrate, Esomeprazole Magnesium dihydrate or to Esomeprazole Sodium according to known prior art methods.

All the preferred embodiments said before can be combined in each combination, always providing the process of the present invention.

The starting material of the process of the present invention, i.e. a mixtures of the optical isomers of the compound of formula (III), can be in ratio 50:50 (w/w) which corresponds to the racemic compound named Omeprazole or, alternatively, can be a mixture of enantiomers having a different ratio which can be prepared by asymmetric oxidation of the substrate named Ufiprazole. In the latter case, after having prepared a mixture of optical isomers of the compound of formula (III) for example with a ratio 80:20 (w/w) of (5) enantiomer versus the (R) enantiomer, applying the process of the present invention is possible to enrich the mixture in terms of Esomeprazole until more than 95% or more than 99% (w/w).

EXPERIMENTAL SECTION

The starting material Omeprazole is a largely commercially available substance. Enantiomerically enriched mixtures of (5) and (R)-Omeprazole can be prepared by asymmetric oxidation of Ufiprazole according to known prior art methods.

Example 1

Preparation of Esomeprazole (S)-(−)-BINOL Complex from DCM/CPME at 20-25° C.—Entry 6 of Table 1

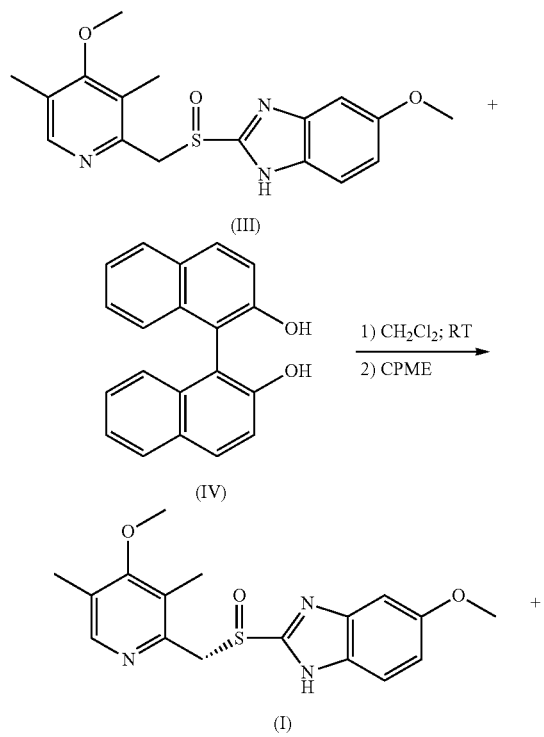

-continued

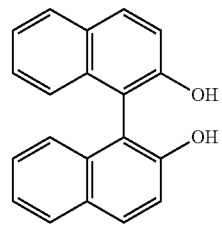

To an enantiomerically enriched mixture of S and R enantiomers with ratio 56.46:43.54 of Omeprazole (15.0 g, 43.4 mmol) in dichloromethane (75.0 ml; 5 volumes) (abbreviated DCM) was added (S)-BINOL (18.65 g, 65.1 mmol; 1.50 mol. equiv) and the resulting mixture was stirred at 20-25° C. for 10 min until complete dissolution was observed. Cyclopentyl methyl ether (75.0 ml) (abbreviated CPME) was then added at 20-25° C. in 55 min (precipitation occurred at the end of the addition) and the resulting mixture was stirred at 20-25° C. for 3 h. The slurry was filtered and the filter-cake was washed with cyclopentyl methyl ether (2×15.0 ml). The collected solid was dried at 35° C. to afford 10.8 g of Esomeprazole (S)-BINOL complex (molar yield 69.7%). The content of (R)-Omeprazole is 0.58% and the content of total impurities is 0.27%. More data on the product and its impurity profile are in Entry 6 of Table 1.

Example 2

Preparation of Esomeprazole (S)-(−)-BINOL Complex from DCM/CPME at 0-3° C.—Entry 7 of Table 1

To an enantiomerically enriched mixture of S and R enantiomers with ratio 56.46:43.54 of Omeprazole (15.0 g, 43.4 mmol) in dichloromethane (75.0 ml) was added (S)-BINOL (18.65 g, 65.1 mmol) and the resulting mixture was stirred at 20-25° C. for 10 min until complete dissolution was observed. The solution was cooled down to 0-3° C., cyclopentyl methyl ether (75.0 ml) was then added at 0-3° C. in 60 min (precipitation occurred 1.5 h after the end of the addition) and the resulting mixture was stirred at 0-3° C. for 3 h. The slurry was filtered and the filter-cake was washed with cyclopentyl methyl ether (2×20.0 ml). The collected solid was dried at 35° C. to afford 8.4 g of Esomeprazole (S)-BINOL complex (molar yield 54.2%). More data on the product are in Entry 7 of Table 1.

Example 3

Preparation of Esomeprazole (S)-(−)-BINOL Complex from DCM/IPE at 20-25° C.—Entry 8 of Table 1

To an enantiomerically enriched mixture of S and R enantiomers (56.46:43.54) of Omeprazole (15.0 g, 43.4 mmol) in dichloromethane (75.0 ml) was added (S)-BINOL (18.65 g, 65.1 mmol) and the resulting mixture was stirred at 20-25° C. for 10 min until complete dissolution was observed. Diisopropyl ether (75.0 ml) (abbreviated IPE) was then added at 20-25° C. in 55 min (precipitation occurred at the end of the addition) and the resulting mixture was stirred at 20-25° C. for 3.5 h. The slurry was filtered and the filter-cake was washed with diisopropyl ether (2×15.0 ml). The collected solid was dried at 35° C. to afford 14.7 g of Esomeprazole (S)-BINOL complex (molar yield 94.9%). More data on the product are in Entry 8 of Table 1.

Example 4

Preparation of Esomeprazole (S)-(−)-BINOL Complex from DCM/MTBE at 20-25° C.—Entry 10 of Table 1

To an enantiomerically enriched mixture of S and R enantiomers (56.46:43.54) of Omeprazole (15.0 g, 43.4 mmol) in dichloromethane (75.0 ml) was added (S)-BINOL (18.65 g, 65.1 mmol) and the resulting mixture was stirred at 20-25° C. for 10 min until complete dissolution was observed. Methyl tert-butyl ether (75.0 ml) (abbreviated MTBE) was then added at 20-25° C. in 60 min and the resulting mixture was stirred at 20-25° C. for 3.0 h. The slurry was filtered and the filter-cake was washed with methyl tert-butyl ether (3×15.0 ml). The collected solid was dried at 35° C. to afford 12.2 g of Esomeprazole (S)-BINOL complex (molar yield 78.8%). More data on the product are in Entry 10 of Table 1.

Example 5

Preparation of Esomeprazole (S)-(−)-BINOL Complex from DCM/MTBE at 0-5° C.—Entry 11 of Table 1

To an enantiomerically enriched mixture of S and R enantiomers (56.46:43.54) of Omeprazole (15.0 g, 43.4 mmol) in dichloromethane (75.0 ml) was added (S)-BINOL (18.65 g, 65.1 mmol) and the resulting mixture was stirred at 20-25° C. for 10 min until complete dissolution was observed. The solution was cooled down to 0-5° C., methyl tert-butyl ether (75.0 ml) was then added at 0-5° C. in 60 min and the resulting mixture was stirred at 0-5° C. for 3 h. The slurry was filtered and the filter-cake was washed with methyl tert-butyl ether (3×15.0 ml). The collected solid was dried at 35° C. to afford 12.2 g of Esomeprazole (S)-BINOL complex (78.8%). More data on the product are in Entry 11 of Table 1.

Example 6

Preparation of Esomeprazole (S)-(−)-BINOL Complex from DCM/DBE at 20-25° C.—Entry 12 of Table 1

To an enantiomerically enriched mixture of S and R enantiomers (56.46:43.54) of Omeprazole (15.0 g, 43.4 mmol) in dichloromethane (75.0 ml) was added (S)-BINOL (18.65 g, 65.1 mmol) and the resulting mixture was stirred at 20-25° C. for 10 min until complete dissolution was observed. Dibuthyl ether (75.0 ml) (abbreviated DBE) was then added at 20-25° C. in 60 min and the resulting mixture was stirred at 20-25° C. for 3 h. The slurry was filtered and the filter-cake was washed with dibuthyl ether (3×15.0 ml). The collected solid was dried at 35° C. to afford 14.5 g of Esomeprazole (S)-BINOL complex (molar yield 93.6%). More data on the product are in Entry 12 of Table 1.

Example 7

Preparation of Esomeprazole (S)-BINOL Complex According to WO12/104863 Example 2—Comparative Example. Entry 4 of Table 1

To an enantiomerically enriched mixture of S and R enantiomers (51.15:48.85) of Omeprazole (20.0 g, 57.9 mmol) in dichloromethane (49.4 ml) was added (S)-BINOL (18.0 g, 62.9 mmol) and the resulting mixture was stirred at 20-25° C. for 15 min until complete dissolution was observed. Toluene (296.4 ml) was then added at 20-25° C. in 15 min and the resulting mixture was stirred at 20-25° C. for 4 h. The slurry was filtered and the filter-cake was washed with DCM/toluene 1:6 (42 ml). The collected solid was dried at 35° C. to afford 14.6 g of Esomeprazole (S)-BINOL complex (78.0%). More data on the product are in Entry 4 of Table 1.

Example 8

Preparation of Esomeprazole (S)-BINOL Complex from DCM/MTBE at 0-5° C. Entry 5 of Table 1

To an enantiomerically enriched mixture of S and R enantiomers (51.15:48.85) of Omeprazole (20.0 g, 57.9 mmol) in dichloromethane (100.0 ml) was added (S)-BINOL (24.9 g, 87.0 mmol) and the resulting mixture was stirred at 20-25° C. for 10 min until complete dissolution was observed. The solution was cooled down to 0-5° C., methyl tert-butyl ether (100.0 ml) was then added at 0-5° C. in 60 min and the resulting mixture was stirred at 0-5° C. for 3 h. The slurry was filtered and the filter-cake was washed with methyl tert-butyl ether (2×20.0 ml). The collected solid was dried at 40° C. to afford 15.0 g of Esomeprazole (S)-BINOL complex (80.2%). More data on the product are in Entry 5 of Table 1.

Example 9

Table of Comparison of the Invention with the Prior Art

TABLE 1

| | Starting material Mixture of S and R enantiomers | | | | | | Process for preparation Esomeprazole (S)-BINOL complex | | | |
|---|---|---|---|---|---|---|---|---|---|---|
| Entry | Input (g) | Omeprazole (%) | N-oxide (%) | Sulfone (%) | Ufiprazole (%) | Total impurities (%) | R (%) | Prior Art or invention | Solvent mixture | (S)-BINOL (equiv) | T (° C.) step B/T (° C.) step C |
| 1 | 20 | 98.58 | 0.05 | 0.42 | 0.01 | 1.42 | 37.34 | U.S. Pat. No. 8,404,853 ex.1 | Tol/Cy | 1.50 | 60/0-5 |
| 2 | 20 | 98.58 | 0.05 | 0.42 | 0.01 | 1.42 | 37.34 | Invention | DCM/MTBE | 1.50 | 0-5 |
| 3 | 20 | 99.53 | 0.02 | 0.15 | 0.05 | 0.47 | 48.85 | U.S. Pat. No. 8,404,853 ex.1 | Tol/Cy | 1.50 | 60/0-5 |
| 4 | 20 | 99.53 | 0.02 | 0.15 | 0.05 | 0.47 | 48.85 | WO12/104863 ex.2 | DCM/Tol | 1.09 | 20-25 |
| 5 | 20 | 99.53 | 0.02 | 0.15 | 0.05 | 0.47 | 48.85 | Invention | DCM/MTBE | 1.50 | 0-5 |
| 6 | 15 | 99.29 | N/D | 0.54 | 0.17 | 0.71 | 43.54 | Invention | DCM/CPME | 1.50 | 20-25 |
| 7 | 15 | 99.29 | N/D | 0.54 | 0.17 | 0.71 | 43.54 | Invention | DCM/CPME | 1.50 | 0-3 |

TABLE 1-continued

| | | | | | | | | | | | |
|---|---|---|---|---|---|---|---|---|---|---|---|
| 8 | 15 | 99.29 | N/D | 0.54 | 0.17 | 0.71 | 43.54 | Invention | DCM/IPE | 1.50 | 20-25 |
| 9 | 15 | 99.29 | N/D | 0.54 | 0.17 | 0.71 | 43.54 | Invention | DCM/IPE | 1.50 | 0-3 |
| 10 | 15 | 99.29 | N/D | 0.54 | 0.17 | 0.71 | 43.54 | Invention | DCM/MTBE | 1.50 | 20-25 |
| 11 | 15 | 99.29 | N/D | 0.54 | 0.17 | 0.71 | 43.54 | Invention | DCM/MTBE | 1.50 | 0-5 |
| 12 | 15 | 99.29 | N/D | 0.54 | 0.17 | 0.71 | 43.54 | Invention | DCM/DBE | 1.50 | 20-25 |
| 13 | 15 | 99.29 | N/D | 0.54 | 0.17 | 0.71 | 43.54 | Invention | DCM/DBE | 1.50 | 0-5 |

| | Isolated Esomeprazole (S)-BINOL Complex | | | | | | | |
|---|---|---|---|---|---|---|---|---|
| Entry | Amount (g) | Yield (%) | Esomeprazole (%) | N-oxide (%) | Sulfone (%) | Ufiprazole (%) | (S)-BINOL (%) | Total impurities (%) | R (%) |
| 1 | 23.9 | 104.3 | 47.96 | N/D | 0.31 | N/D | 51.59 | 0.45 | 3.04 |
| 2 | 18.0 | 78.5 | 53.27 | N/D | 0.14 | N/D | 46.45 | 0.28 | 3.65 |
| 3 | 18.1 | 96.7 | 51.50 | 0.03 | 0.16 | 0.04 | 47.12 | 1.38 | 2.26 |
| 4 | 14.6 | 78.0 | 53.84 | N/D | 0.12 | 0.01 | 46.02 | 0.14 | 2.74 |
| 5 | 15.0 | 80.2 | 53.75 | N/D | 0.06 | N/D | 46.18 | 0.07 | 4.31 |
| 6 | 10.8 | 69.7 | 53.98 | N/D | 0.24 | N/D | 45.75 | 0.27 | 0.58 |
| 7 | 8.4 | 54.2 | 54.55 | N/D | 0.19 | 0.01 | 45.21 | 0.24 | 2.60 |
| 8 | 14.7 | 94.9 | 53.67 | N/D | 0.38 | 0.02 | 45.87 | 0.46 | 4.19 |
| 9 | 15.4 | 99.4 | 53.28 | N/D | 0.37 | 0.02 | 46.27 | 0.45 | 5.27 |
| 10 | 12.2 | 78.8 | 53.83 | N/D | 0.21 | N/D | 45.92 | 0.25 | 1.00 |
| 11 | 12.2 | 78.8 | 53.45 | N/D | 0.25 | 0.02 | 46.25 | 0.30 | 2.09 |
| 12 | 14.5 | 93.6 | 53.90 | N/D | 0.38 | 0.02 | 45.69 | 0.41 | 3.44 |
| 13 | 12.7 | 82.0 | 53.81 | N/D | 0.33 | 0.01 | 45.83 | 0.36 | 2.53 |

Legenda:

The amounts indicated in the table 1 for Esomeprazole and (S)-BINOL are expressed in percentage weight/weight, while the other percentage are expressed as Area %.
Tol=toluene; Cy=cyclohexane; DCM=dichloromethane; MTBE=methyl-t-buthyl ether; CPME=cyclopropylmethlyether, IPE=Diisopropylether; DBE=dibuthylether.

The percentage values for Esomeprazole and (S)-BINOL of the Table 1 are expressed as percentage weight/weight not in percentual area (A %).

The molecular weight of Esomeprazole is 345.42, that of (S)-(−)-BINOL is 286.33 and that of Esomeprazole (S)-(−)-BINOL complex is 631.74. Thus, the theoretical percentage expressed as weight by weight of Esomeprazole versus Esomeprazole (S)-(−)-BINOL complex is 54.68%, while the theoretical percentage of (S)-(−)-BINOL is 45.32%.

Analyzing the results of table 1 it has been found that only the method according to the present invention and the method disclosed in WO2012/104863 allow the preparation of Esomeprazole (S)-(−)-BINOL complex having the right amount of (S)-(−)-BINOL, while the product prepared according to the teachings of U.S. Pat. No. 8,404,853 contains an extra amount of (S)-(−)-BINOL. This is probably due to the fact that the anti-solvent used, in that case cyclohexane, precipitates both the Esomeprazole (S)-(−)-BINOL complex and the excess of (S)-(−)-BINOL used.

By comparison of entry 5 with entry 4 (WO2012/104863) and also with the other entries 1-3, it is possible to see the clear effect of the process of the present invention, indeed the content of the total impurities of the product prepared according to the process of the present invention is at least a half of that of the product prepared according to prior processes. This is mainly due to the high efficiency of the process of the present invention in the removal of the sulfone impurity. By analyzing the table 1 it is indeed possible to see that the process of the present invention is much more effective in removing the sulfone impurity than the known prior art methods. Moreover the process of the present invention does not provide degradation products such as the N-oxide impurity that would affect the purity of the Esomeprazole (S)-(−)-BINOL complex.

Furthermore, the Esomeprazole (S)-(−)-BINOL complex prepared according to the method of present invention is an off-white solid, but more clear than the off-white solid prepared according to WO2012/104863 and much more clear in comparison with the product obtained by the process disclosed in U.S. Pat. No. 8,404,853 which is grey/purple.

Finally, Esomeprazole (S)-(−)-BINOL complex prepared according to the method of the present invention is the purest product in terms of chemical purity.

Example 10

Analytical Method Used for the Determination of the Chemical Purity by HPLC of the Mixtures of the Isomers of the Compound of Formula (III) and of Esomeprazole (S)-(−)-Binol Complex of Table 1

Cromatographic Conditions:
Column: Phenomenex Kinetex XDB-C18, 100×4.6 mm, 5 µm with pre-column.
Temp. column: 45° C.
Mobil phase A: $CH_3COONH_4$ 15 mM in $H_2O$
Mobil phase B: ACN

| Gradient: | | |
|---|---|---|
| Time (min) | % A | % B |
| 0 | 82 | 18 |
| 6.5 | 70 | 30 |
| 10 | 40 | 60 |
| 12 | 82 | 18 |

Post-run time: 3 minutes
Flux: 2.2 mL/min
Detector: UV a 280 nm, bw 4 nm
Injection volume: 5 µL
Diluent: Methanol
Analysis time: 12 min
Note: Equip the HPLC with 0.005" PEEK Tubing to minimize the dwell volume.

Preparation of the Solution Standard

In a flask of 50 mL to introduce an exact amount about circa: 15 mg di Ufiprazole, 15 mg di Sulfone impurity, 15 mg di (S)-Binol;

To dissolve with diluent, to add 100 μL di Triethylamine and to dilute to volume with diluent.

The retention times should be approximately as follow:

| Compund | RT (min) | RRT | RRF |
|---|---|---|---|
| Omeprazole | 5.1 | 1.00 | 1.00 |
| Sulfone impurity | 5.5 | 1.07 | 1.00 |
| Ufiprazole | 7.7 | 1.50 | 1.15 |
| (S)-Binol | 9.7 | 1.90 | 0.78. |

The invention claimed is:

1. A process for preparing an Esomeprazole (S)-(−)-BINOL complex of formula (I):

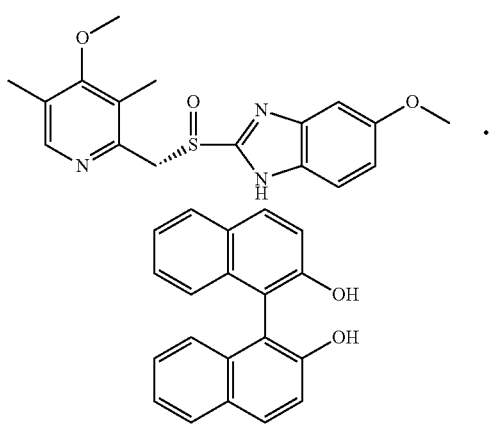

comprising the following steps:

A. providing a mixture of optical isomers of the compound of formula (III):

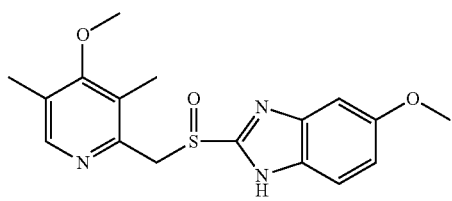

wherein the chiral center is on the sulfur atom, in dichloromethane;

B. adding to the mixture of step A from 0.8 to 3.0 molar equivalents of (S)-(−)-BINOL;

C. adding an ethereal solvent containing from 5 to 10 carbon atoms;

D. stirring; and

E. isolating the Esomeprazole (S)-(−)-BINOL complex of formula (I).

2. The process according to claim 1, wherein the mixture of the optical isomers in step A is suspended in from 4 to 6 volumes of dichloromethane, as compared to the volume of the compound of formula (III).

3. The process according to claim 1, wherein (S)-(−)-BINOL is added in the amount of from 0.8 to 1.8 molar equivalents in step B.

4. The process according to claim 3, wherein (S)-(−)-BINOL is added in the amount of about 1.5 molar equivalents.

5. The process according to claim 1, further comprising a step of stirring at a temperature of between 0° C. and 40° C. after step B.

6. The process according to claim 5, wherein the temperature is from 15° C. to 25° C.

7. The process according to claim 5, wherein the stirring is carried out for a period of time between 5 and 60 minutes.

8. The process according to claim 1, wherein the ethereal solvent in step C is added in the amount of from 4 to 6 volumes, compared to the amount of the compound of formula (III).

9. The process according to claim 1, wherein step D is carried out at temperature of from 15° C. to 25° C.

10. The process according to claim 9, wherein the stirring is carried out for a period of time between 1 and 4 hours.

11. The process according to claim 1, wherein steps B, C and D are carried out at the same temperature.

12. The process according to claim 1, wherein steps A and B are both carried out at a temperature of between 15° C. and 25° C., and steps C and D are both carried out at a temperature of between 15° C. and 25° C. or at a temperature of between 0° C. and 5° C.

13. The process according to claim 1, wherein the mixture of the optical isomers in step A is suspended in from 4 to 6 volumes of dichloromethane, and wherein the ethereal solvent in step C is added in the volume of from 4 to 6 volumes, as compared to the volume of the compound of formula (III).

14. The process according to claim 1, wherein the ethereal solvent is chosen from methyl-t-buthylether, diisopropylether, methylisobuthylether, or cyclopentyl methyl ether.

15. The process according to claim 1, further comprising a conversion of the Esomeprazole (S)-(−)-BINOL complex to Esomeprazole free acid, or the conversion of the complex to Esomeprazole Magnesium trihydrate, Esomeprazole Magnesium dihydrate, or Esomeprazole Sodium.

* * * * *